United States Patent
Kobayashi et al.

(10) Patent No.: US 7,351,831 B2
(45) Date of Patent: Apr. 1, 2008

(54) PROCESS FOR ASYMMETRIC INTRAMOLECULAR [3+2] CYCLO-ADDITION OF HYDRAZONES

(75) Inventors: Shu Kobayashi, Tokyo (JP); Yasuhiro Yamashita, Tokyo (JP); Haruro Ishitani, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 556 days.

(21) Appl. No.: 10/507,309

(22) PCT Filed: Mar. 11, 2003

(86) PCT No.: PCT/JP03/02862

§ 371 (c)(1),
(2), (4) Date: Nov. 3, 2004

(87) PCT Pub. No.: WO03/076410

PCT Pub. Date: Sep. 18, 2003

(65) Prior Publication Data

US 2005/0165237 A1 Jul. 28, 2005

(30) Foreign Application Priority Data

Mar. 11, 2002 (JP) ............... 2002-066161

(51) Int. Cl.
*C07D 471/04* (2006.01)
(52) U.S. Cl. .............. 546/119; 546/17; 548/357.5; 548/360.1; 548/360.5
(58) Field of Classification Search .......... 546/17, 546/119; 548/357.5, 360.1, 360.5
See application file for complete search history.

(56) References Cited

OTHER PUBLICATIONS

Kobayashi, Shu et al., "Asymmetric Intramolecular [3+2] Cycloaddition Reactions of Acylhydrazones/Olefins Using a Chiral Zirconium Catalyst," *Journal of American Chemical Society* (2002), 124(46), pp. 13678 to 13679.

Fouchet, B. et al., "(3+2) Intramolecular Cationic Cycloadditions and 1,3-Dipolar Cycloadditions of Phenylhydrazones", *Tetrahedron Letters* (1981), 22(14), p. 1333-6.

Kobayashi, Shu et al., "Chiral Catalyst Optimization Using Both Solid-phase and Liquid-phase Methods in Asymmetric Aza Diels-Alder Reactions," *Organic Letters* (2000), 2(9), pp. 1225 to 1227.

Sakane, Soichi et al., "Asymmetric Cyclization of Unsaturated Aldehydes Catalyzed by a Chiral," *Tetrahedron* (1986), 42(8), p. 2203-9.

*Primary Examiner*—Bernard Dentz
(74) *Attorney, Agent, or Firm*—Wenderoth, Lind Ponack, L.L.P.

(57) ABSTRACT

An intramolecular [3+2] cycloaddition reaction of a hydrazone is carried out under a mild condition with a high stereoselectivity and yield by reacting a hydrazone derivative in the presence of an asymmetric catalyst system obtained by mixing a zirconium alkoxide represented by the following formula (I):

$$Zr(OR)_4 \quad (I)$$

(wherein R is a hydrocarbon group which may have a substituent) with a binaphthol derivative represented by the following formula (II):

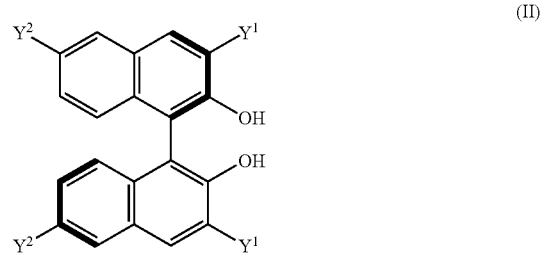

(wherein $Y^1$ and $Y^2$ are each identical or different and denote a hydrogen atom or a halogen atom, and at least one of $Y^1$ and $Y^2$ denotes a halogen atom).

5 Claims, No Drawings

PROCESS FOR ASYMMETRIC INTRAMOLECULAR [3+2] CYCLO-ADDITION OF HYDRAZONES

TECHNICAL FIELD

The invention of this application relates to an asymmetric intramolecular [3+2] cycloaddition reaction of a hydrazone derivative. More particularly, the invention of this application relates to a process for an asymmetric intramolecular [3+2] cyclization of a hydrazone derivative under a mild condition with ease and high efficiency.

BACKGROUND ART

In nature, many substances including proteins and the like are optically active substances, and it is known that a specific bioactivity is expressed according to the stereostructure thereof. Also compounds containing a nitrogen atom are found in great number in natural products. Among them, many of the compounds containing a nitrogen atom in the five-membered ring skeleton are considered to largely contribute to the expression of molecular function.

Therefore, it can be said that establishing a stereoselective synthetic method of a nitrogen-containing compound is important in a total synthesis of a bioactive substance, which is the object in the field of medicine, agricultural chemical, flavor or the like.

As one of the useful processes for constructing a nitrogen-containing five-membered ring skeleton, there is a [3+2] cycloaddition reaction, which has been studied since long time ago. Among them, a cycloaddition reaction using a 1,3-dipole with a high reactivity such as a nitrone has been widely studied, and an example of a catalytic asymmetric reaction using an asymmetric Lewis acid has been reported. Meanwhile, as a [3+2] cycloaddition reaction of an aryl or an acylhydrazone, a cycloaddition reaction of an alkene with an aryl or an acylhydrazone using a protonic acid as a catalyst was reported for the first time in 1970 by Hesse. In addition, it was reported that this reaction proceeds thermally in 1979 by Griggs et al. Since then, several reactions of the same kind have been reported, however, all needs a reaction under a condition with a strong acid or under a thermal condition, and a reaction under a mild condition with the use of a Lewis acid was not known in the past.

Meanwhile, the inventors of this application have reported, until now, various catalytic asymmetric synthesis reactions of a nitrogen-containing compound including the asymmetric Mannich reaction, the aza Diels-Alder reaction, the asymmetric Strecker reation and the like with the use of a chiral zirconium catalyst. Also, at this late date, they have found that intermolecular [3+2] cycloaddition reaction of a hydrazone takes place even under a mild condition with a high yield and a high diastereoselectivity by using a catalytic amount of 10 mol % of zirconium triflate, which has been reported.

However, the fact is that an easy process in which an intramolecular asymmetric cycloaddition reaction of a hydrazone is carried out under a mild condition was not realized. An intramolecular [3+2] asymmetric cycloaddition reaction can not only efficiently construct a polycyclic structure, but also derive a cyclic 1,3-diamine by cleaving the N—N bond of the product, therefore, it can be said that its usability is high.

The invention of this application has been conducted in view of the above-mentioned circumstances, and aims at overcoming the limits of the prior art and providing a process for carrying out an asymmetric intramolecular [3+2] cycloaddition reaction of a hydrazone under a common mild condition with a high stereoselectivity and yield.

DISCLOSURE OF THE INVENTION

In order to solve the problems as above, the invention of this application firstly provides a process for an asymmetric intramolecular [3+2] cycloaddition reaction of a hydrazone characterized by reacting a hydrazone derivative represented by the following formula (III):

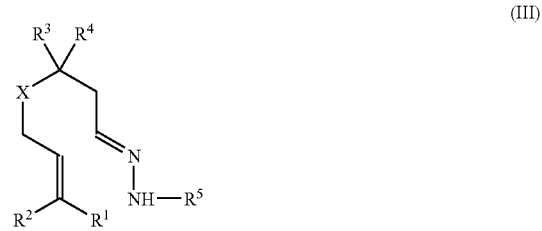

(wherein $R^1$, $R^2$, $R^3$, $R^4$ and $R^5$ are each identical or different and denote a hydrogen atom or a hydrocarbon group which may have a substituent or a hetero atom, $R^1$ and $R^2$, $R^3$ and $R^4$ may be linked to form a ring by a hydrocarbon chain which may have a substituent or a hydrocarbon chain which has a hetero atom, and X denotes a hetero atom or a hydrocarbon chain which may have a substituent or a hetero atom) in the presence of an asymmetric catalyst system obtained by mixing a zirconium alkoxide represented by the following formula (I):

$$Zr(OR)_4 \qquad (I)$$

(wherein R is a hydrocarbon group which may have a substituent) with a binaphthol derivative represented by the following formula (II):

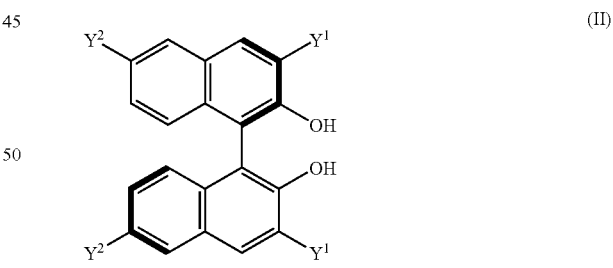

(wherein $Y^1$ and $Y^2$ are each identical or different and denote a hydrogen atom or a halogen atom, and at least one of $Y^1$ and $Y^2$ denotes a halogen atom).

Also, the invention of this application secondly provides the above-mentioned process for an asymmetric intramolecular [3+2] cycloaddition reaction, which is carried out in the coexistence of a primary alcohol, and thirdly provides the process for an asymmetric intramolecular [3+2] cycloaddition reaction in which the primary alcohol is an n-propanol. In addition, the invention of this application fourthly provides the process for an asymmetric intramolecular [3+2] cycloaddition reaction, by which a compound represented by the following formula (IV):

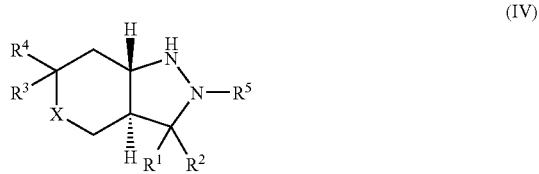

is synthesized.

Also, the invention of this application fifthly provides the process for an asymmetric intramolecular [3+2] cycloaddition reaction according to any one of the above, in which the zirconium alkoxide used in the catalyst system is $Zr(O^tBu)_4$ or $Zr(OPr)_4$.

BEST MODE FOR CARRYING OUT THE INVENTION

The inventors of this application found that an intermolecular [3+2] addition reaction of hydrozone efficiently proceeds even under a mild condition, for example, at room temperature or in an organic solvent, by using a catalytic amount of zirconium triflate. They continued further dedicated studies on expansion to a catalytic asymmetric reaction, and as a result, the invention of this application has been worked out.

Namely, in the process for an asymmetric intramolecular [3+2] cycloaddition reaction of the invention of this application, an intramolecular [3+2] cyclization of a hydrazone derivative stereoselectively takes place by using what is obtained by mixing a zirconium alkoxide represented by the following formula (I):

$$Zr(OR)_4 \quad (I)$$

(wherein R is a hydrocarbon group which may have a substituent) with a binaphthol derivative represented by the following formula (II):

(wherein $Y^1$ and $Y^2$ are each identical or different and denote a hydrogen atom or a halogen atom, and at least one of $Y^1$ and $Y^2$ denotes a halogen atom) as a catalyst system.

As the hydrazone, there are a ketone hydrazone represented by $RR'C=NNH_2$ and an aldehyde hydrazone represented by $RCH=NNH_2$ in general. In the process for an asymmetric intramolecular [3+2] cycloaddition reaction of the invention of this application, the hydrazone derivative may be any, and various derivatives including a ketone hydrazone derivative of $RR'C=N-NH-R''$, an aldehyde hydrazone derivative of $RCH=N-NH-R''$ and the like may be taken into consideration. Preferred examples include, for example, a compound represented by the following formula (III).

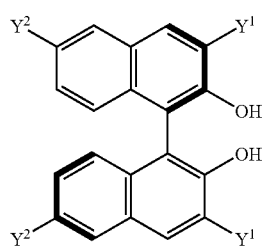

In this formula, $R^1$, $R^2$, $R^3$, $R^4$ and $R^5$ are each identical or different, and denote a hydrogen atom or a hydrocarbon group which may have a substituent or a hetero atom. Also, $R^1$ and $R^2$, $R^3$ and R4 may be linked to form a ring by a hydrocarbon chain which may have a substituent or a hetero atom. X is a hetero atom or a hydrocarbon chain which may have a substituent or a hetero atom.

As the above-mentioned $R^1$, $R^2$, $R^3$ and $R^4$, there is no particular restriction as long as it does not inhibit an intramolecular [3+2] cyclization of a hydrazone derivative, however, specific examples include an alkyl group such as methyl, ethyl, n-propyl, i-propyl or t-butyl, an aromatic group such as phenyl or naphthyl, and a hydrocarbon group having a substituent containing a halogen atom or O, N, S. Among them, preferred examples include a lower alkyl group such as methyl or ethyl. In the case where $R^1$ and $R^2$, $R^3$ and $R^4$ form a ring respectively, examples include —$CH_2CH_2CH_2CH_2$—, —$CH_2CH_2CH_2CH_2CH_2$—, —$CH_2CH(CH_3)CH_2CH_2$—, $CH_2CH_2OCH_2CH_2$—, $OCH_2CH_2O$—, $SCH_2CH_2S$— and the like.

Examples of the X include, for example, forms of —$CH_2$—, —$CH(CH_3)$—, —O—, —S— and the like.

Meanwhile, as the $R^5$, it may be the same as $R^1$ to $R^4$, however, among them, preferred examples include a hydrocarbon group having a hetero atom such as O, N or S, such as a carbonyl group, a nitro group or a sulfonic acid group, and an aromatic group. Examples of the hydrazone derivative include the one whose $R^5$ is an acyl group, for example, a compound such as —CO—Me, —CO—Et, —CO—Pr, —CO—Ph or —CO—Ph—$NO_2$. More specifically, preferred examples include the one whose $R^5$ has a benzoyl group with a 4-nitro group, a benzoyl group without a 4-nitro group or a benzoyl group with a substituent other than a 4-nitro group.

In the process for an asymmetric intramolecular [3+2] cycloaddition reaction of the invention of this application as mentioned above, these substituents may be arbitrarily selected according to the structure of a target nitrogen-containing compound.

According to the process for an asymmetric intramolecular [3+2] cycloaddition reaction of the invention of this application, for example, an optically active nitrogen-containing cyclic compound of the following formula (IV):

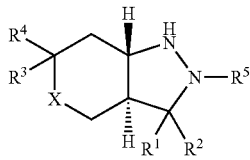

can be obtained.

In the reaction process of the invention of this application which enables a synthesis of such a compound, a hydrazone derivative may be reacted in the presence of a catalyst system as mentioned above, and the reaction condition is not particularly limited. Particularly, however, in the case where a primary alcohol coexists in a reaction system, the reaction yield or stereoselectivity will be increased, therefore, it is preferable. In this case, the kind or amount of the primary alcohol to be added is not limited. For example, 5 to 10 equivalent weight of n-propanol relative to the binaphthol derivative of the above-mentioned (II) may be added.

In the asymmetric intramolecular [3+2] cycloaddition reaction of the invention of this application, other reaction conditions are not particularly limited, however, it is characterized in that an asymmetric intramolecular [3+2] cycloaddition reaction proceeds with a high yield and stereoselectivity even under a mild condition, for example, at a reaction temperature in the vicinity of room temperature or in an organic solvent such as dichloromethane. Examples of the reaction solvent include various organic solvents, however, preferred examples include dichloromethane, benzene, fluorobenzene, toluene and the like. As mentioned above, the reaction yield or stereoselectivity is further improved by adding a primary alcohol to the reaction solvent, which is preferable.

It is needless to say that a nitrogen-containing compound produced by the process of the invention of this application may be further reacted and converted by various organic synthesis methods to obtain a desired substance. For example, an optically active 1,3-diamine can be derived by cleaving the N—N bond of a cyclized compound. In addition, after carrying out the process for an asymmetric intramolecular [3+2] cycloaddition reaction of the invention of this application, to purify the product, common procedures such as extraction, separation, filtration, washing and drying may be carried out.

Hereunder, the invention of this application will be explained in more detail by showing Examples. However, it is needless to say that the invention of this application is not limited to the following Examples.

EXAMPLES

Example 1

According to the following reaction formula (A), asymmetric intramolecular [3+2] cycloaddition reactions using various asymmetric catalyst systems shown in Table 1 were carried out.

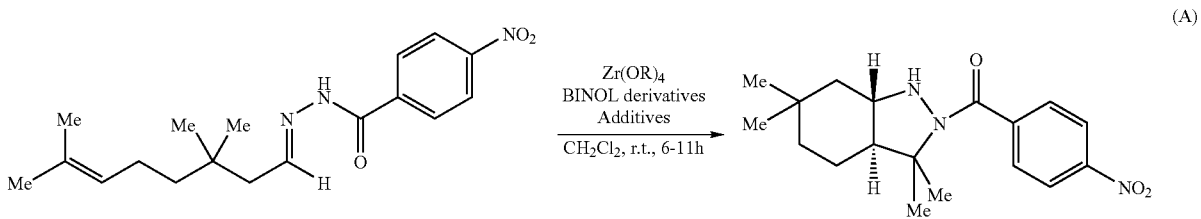

With respect to 4-nitrobenzoyl hydrazone, 1 equivalent weight of aldehyde (as to (S)-Citronellal, a commercially available one was obtained as it was, as to 3,3,7-Trimethyl-6-octenal and 7-Methyl-6-octenal, they were obtained by a method described in a document) relative to a dimethylformamide (DMF) solution of 4-nitrobenzoyl hydrazine was added and stirred for several hours at room temperature until the aldehyde disappeared. Water was added to stop the reaction, and extraction was carried out three times with ethyl acetate. The organic layers were combined and washed with water three times, and with a saturated saline solution once, and dried with anhydrous sodium sulfate. After filtration, the solvent was removed under reduced pressure, then the residue was recrystallized from ethyl acetate-hexane (5:1). When the aldehyde that was a raw material remained, it was purified by silica gel column chromatography, then recrystallized.

The reaction yields and the stereoselectivities are shown in Table 1.

TABLE 1

| Zr(OR)$_4$/mol % | BINOL/mol % | Additive/mol % | Yield (%) | ee/% |
|---|---|---|---|---|
| Zr(O$^t$Bu)$_4$/10 | (R)-3,3'-Br$_2$BINOL/10 | — | 82 | 71 |
| Zr(O$^t$Bu)$_4$/10 | (R)-3,3'-Br$_2$BINOL/20 | — | 86 | 75 |
| Zr(O$^t$Bu)$_4$/10 | (R)-3,3'-Br$_2$BINOL/20 | PrOH/20 | 90 | 72 |
| Zr(O$^t$Bu)$_4$/10 | (R)-3,3'-Br$_2$BINOL/20 | PrOH/50 | 80 | 90 |

TABLE 1-continued

| Zr(OR)₄/mol % | BINOL/mol % | Additive/mol % | Yield (%) | ee/% |
|---|---|---|---|---|
| Zr(O$^t$Bu)₄/10 | (R)-3,3'-Br₂BINOL/20 | PrOH/100 | 90 | 92 |
| Zr(O$^t$Bu)₄/10 | (R)-3,3'-Br₂BINOL/20 | CF₃CH₂OH/50 | 55 | 89 |
| Zr(O$^t$Bu)₄/10 | (R)-3,3'-Br₂BINOL/12 | PrOH/50 | 92 | 93 |
| Zr(O$^t$Bu)₄/10 | (R)-3,3'-Br₂BINOL/12 | PrOH/50, H₂O/20 | 70 | 78 |
| Zr(O$^n$Pr)₄/10 | (R)-3,3'-Br₂BINOL/12 | — | 82 | 92 |

From Table 1, it was confirmed that an asymmetric intramolecular [3+2] cycloaddition reaction of a hydrazone proceeds with a high yield and stereoselectivity by using a catalyst system obtained by mixing Zr(O$^t$Bu)₄ with 3,3'-Br₂BINOL in which Y$^1$ is Br (bromine) and Y$^2$ is a hydrogen atom in the above-mentioned formula (II). Particularly, in the system in which 5 to 10 equivalent weight of alcohol relative to Zr(O$^t$Bu)₄ was added, the yield and the stereoselectivity were significantly improved.

Example 2

The catalyst system in Example 1 was modified, and according to the following reaction formula (B), asymmetric cycloaddition reactions were carried out in the same manner. The results are shown in Table 2.

As is clear from Table 2, in the catalyst system using a BINOL derivative in which both Y$^1$ and Y$^2$ are Br or I in the above-mentioned formula (II), especially a high reaction yield and selectivity were obtained in the case where a primary alcohol was added.

TABLE 2

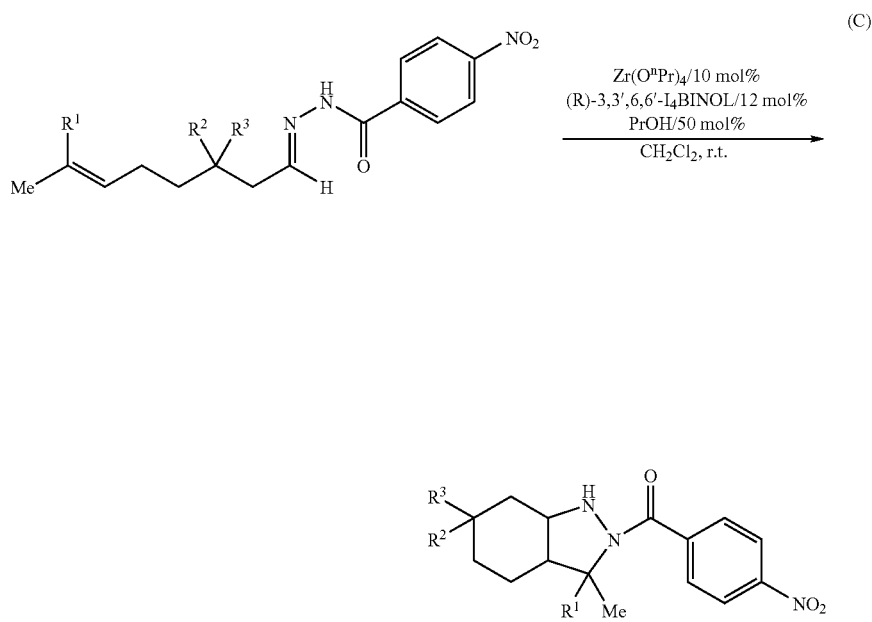

(B)

| BINOL/mol % | Additive/mol % | Time | Yield(%) | ee/% |
|---|---|---|---|---|
| (R)-3,3',6,6'-Br₄BINOL | — | 6 h | 82 | 71 |
| (R)-3,3',6,6'-I₄BINOL | — | 6 h | 86 | 75 |
| (R)-3,3',6,6'-Br₄BINOL | PrOH/50 | 4 h | 90 | 72 |
| (P)-3,3',6,6'-I₄BINOL | PrOH/50 | 4 h | 80 | 90 |
| (R)-3,3',6,6'-I₄BINOL | PrOH/50 | 11 h | 90 | 92 |

Example 3

According to the following formula (C), asymmetric intramolecular [3+2] cycloaddition reactions of various hydrazone derivatives were carried out.

The reaction times, reaction yields and stereoselectivities are shown in Table 3.

TABLE 3

| Run | Hydrazone R¹ | R² | R³ | Time | Yield$^{(cis/trans)}$ | ee/% |
|---|---|---|---|---|---|---|
| 1 | Me | Me | Me | 4.5 h | 99 (<1/>99) | —/99 |
| 2 | Me | Me | Me | 12 h | 87 (<1/>99) | —/90 |
| 3 | Me | Me | H | 20 h | 70 (17/83) | dr cis: 99/1 trans: 98/2 |
| 4 | Me | Me | H | 24 h | 77 (84/16) | dr cis: 8/92 trans: 73/27 |
| 5 | Me | H | H | 64 h | 62 (29/71) | 13/92 |
| 6 | | | | 12 h | 91 (<1/>99) | —/97 |

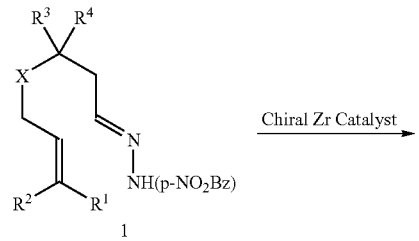

From Table 3, it was confirmed that a high reaction yield and stereoselectivity were obtained in the compound having a substituent in the β-position. In addition, although the reactivity was somewhat lower in the compound without a substituent in the β-position, the enantioselectivity of trans compound was shown to be increased by using a catalyst system that was prepared with 3,3',6,6'-I$_4$BINOL as a binaphthol source.

Meanwhile, in a hydrazone derivative having only one substituent in the β-position, a trans compound was preferentially obtained from (R)-binaphthol, and a cis compound was preferentially obtained from (S)-binaphthol. Furthermore, it was confirmed that in a substrate having a thioketal group in the β-position, the yield and the selectivity are increased.

Example 4

According to the following formula (D), asymmetric intramolecular [3+2] cycloaddition reactions were carried out.

(D)

1a: R¹ = R² = R³ = R⁴ = Me,
  X = —CH$_2$—
1b: R¹ = R² = Me,
  R³ = R⁴ = H, X = —CH$_2$—
1c: R¹ = R² = Me,
  R³ = R⁴ = —SCH$_2$CH$_2$S—,
  X = —CH$_2$—
1d: R¹ = R² = H,
  R³ = R⁴ = —SCH$_2$CH$_2$S—,
  X = —CH$_2$—
1e: R¹ = R² = Me, H,
  R³ = R⁴ = —SCH$_2$CH$_2$S—,
  X = —CH$_2$—
1f: R¹ = R² = —SCH$_2$CH$_2$S—,
  R³ = R⁴ = H, X = —CH$_2$—
1g: R¹ = R² = R³ = R⁴ = Me,
  X = O

-continued

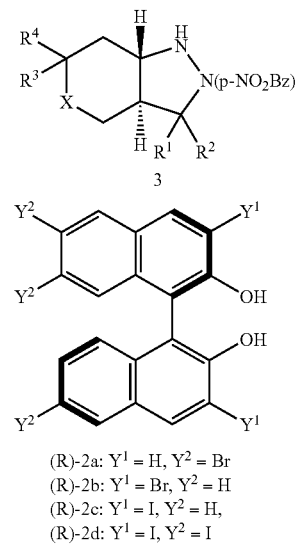

(R)-2a: Y¹ = H, Y² = Br
(R)-2b: Y¹ = Br, Y² = H
(R)-2c: Y¹ = I, Y² = H,
(R)-2d: Y¹ = I, Y² = I

First, 4-nitrobenzoylhydrazone (1a) (R¹=R²=R³=R⁴=Me, X=—CH$_2$—) was reacted with various chiral BINOL catalyst systems. The results are shown in Table 4.

The reaction was carried out in a CH$_2$Cl$_2$ solvent at room temperature for 4 to 11 hours. The denotation b in the table indicates 10 mol %, c indicates 50 mol %, d indicates that benzene was used as a solvent, and e indicates that toluene was used as a solvent.

TABLE 4

| entry | Zr(OR)$_4$$^b$ | BINOL/mol % | additive | yield/% | ee/% |
|---|---|---|---|---|---|
| 1 | Zr(O$^t$Bu)$_4$ | 2a/20 | — | 35 | 9 |
| 2 | Zr(O$^t$Bu)$_4$ | 2b/20 | — | 86 | 75 |
| 3 | Zr(O$^t$Bu)$_4$ | 2b/12 | PrOH$^c$ | 92 | 93 |
| 4 | Zr(OPr)$_4$ | 2b/12 | — | 82, 56$^d$, 86$^e$ | 92, 93$^d$, 95$^e$ |
| 5 | Zr(OPr)$_4$ | 2c/12 | — | 86 | 92 |
| 6 | Zr(OPr)$_4$ | 2d/12 | PrOH$^c$ | 99 | 96 |

Next, using a catalyst system of Zr(OPr)$_4$ (10 mol %), (R)-2d (12 mol %) and PrOH (50 mol %), asymmetric intramolecular cycloaddition reactions of various hydrazone compounds were carried out at room temperature. The results are shown in Table 5.

Incidentally, in entries 5 and 6, (R)-2C was used as BINOL. In addition, the denotation b in the table indicates that the concentration of the catalyst was 5 mol %, C indicates that the concentration of the catalyst was 20 mol %, d indicates that it was crude, e indicates that the yield was calculated on the basis of the starting material compound (4), f indicates that the reaction temperature was 40° C., and g indicates that the reaction temperature was 60° C.

TABLE 5

| entry | hydrazone | solvent, time | yield/% (cis/trans) | ee/% (trans) |
| --- | --- | --- | --- | --- |
| 1 | 1a | CH$_2$Cl$_2$, 4.5 h | 99 (<1/>99) | 96 |
| 2[b] | 1a | CH$_2$Cl$_2$, 12 h | 87 (<1/>99) | 90 |
| 3[b] | 1a | benzene, 28 h | 70 (<1/>99) | 95 |
| 4[c] | 1b | benzene-CH$_2$Cl$_2$, 64 h | 62 (29/71) | 92 |
| 5[c] | 1c | CH$_2$Cl$_2$, 12 h | 91 (<1/>99) | 97 |
| 6 | 1f[d] | benzene, 1 h | 57[e] (<1/>99) | 72 |
| 7[e,f] | 1g | benzene, 21 h | 38 (<1/>99) | 81 |
| 8[e,g] | 1h | benzene, 1 h | 73 (11/89) | 90 |

1 h

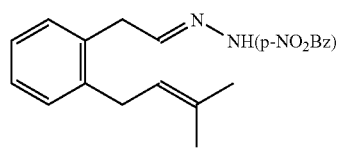

4

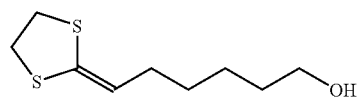

The asymmetric cyclic compounds shown with the following identification values were obtained corresponding to the hydrazone compounds that were reaction targets.

(3aS, 7aS)-3,3,6,6-Tetramethyl-2-(p-nitrobenzoyl)indazolidine (3a): [α]$_D^{29}$ −40.5 (c 1.01, CHCl$_3$, 99% ee (after recrystallization)). IR [cm$^{-1}$] (KBr) 3466, 2905, 2870, 1636, 1601, 1518, 1466, 1397, 1385, 1345, 1310. $^1$H NMR (CDCl$_3$) δ=0.92-1.02 (m, 1H), 0.96 (s, 3H), 1.00 (s, 3H), 1.21-1.28 (m 2H), 1.43 (ddd, 1H, J=12, 12, 4.6 Hz), 1.47 (s, 3H), 1.61 (m, 2H), 1.65 (s, 3H), 1.75 (dd, 1H, J=12, 3.4 Hz), 2.84 (ddd, 1H, J=13, 12, 3.4 Hz), 3.28 (d, 1H, J=13 Hz), 7.33 (d, 2H, J=8.6 Hz), 8.19 (d, 2H, J=8.6 Hz); $^{13}$C NMR (CDCl$_3$) δ=19.6, 20.4, 25.6, 25.9, 31.9, 32.7, 38.8, 41.3, 57.7, 60.9, 65.3, 122.8, 128.8, 143.8, 147.8, 165.5. MS (m/z) 331 (M$^+$). Anal. calcd for C$_{18}$H$_{25}$N$_3$O$_3$: C, 65.23; H, 7.60; N, 12.68, found: C, 65.24; H, 7.79; N, 12.72. HPLC: Daicel Chiralpak AD, hexane/$^i$PrOH=9/1, flow rate=1.0 mL/min: t$_R$=20.8 min (3aS, 7aS), t$_R$=39.4 min (3aR, 7aR).

trans-3,3-Dimethyl-2-p-nitrobenzoyl)indazolidine (3b): IR [cm$^{-1}$] (KBr) 3107, 1630, 1600, 1523, 1455, 1405, 1384, 1344. $^1$H NMR (CDCl$_3$) trans isomer: δ=1.05 (m, 1H), 1.20-1.35 (m, 4H), 1.44 (s, 3H), 1.64 (s, 3H), 1.75 (m, 1H), 1.85-1.90 (m, 2H), 2.05 (m, 2H), 2.62 (br, 1H), 3.79 (br, 0.8H), 7.72 (d, 1H, J=8.8 Hz), 8.19 (d, 1H, J=8.8 Hz); $^{13}$C NMR (CDCl$_3$) trans isomer; δ=19.5, 24.2, 24.4, 25.5, 26.0, 28.7, 60.3, 60.8, 65.4, 122.9, 128.8, 143.9, 147.9, 165.6. MS (m/z) 303 (M$^+$). Anal. calcd for C$_{16}$H$_{21}$N$_3$O$_3$: C, 63.35; H, 6.98; N, 13.85, found: C, 63.41; H, 6.93; N, 13.58. HPLC: Daicel Chiralcel OJ, hexane/$^i$PrOH=19/1, flow rate=1.0 mL/min: t$_R$=44.5 min (minor), t$_R$=54.2 min (major).

trans-6,6-Ethylenedithio-3,3-Dimethyl-2-(p-nitrobenzoyl)indazolidine (3c): IR [cm$^{-1}$] (KBr) 3438, 3206, 1625, 1596, 1524, 1422, 1345. $^1$H NMR (CDCl$_3$) δ=1.33 (dt, 1H, J=12, 3.1 Hz), 1.47 (s, 3H), 1.55 (m, 1H), 1.67 (s, 3H), 1,64-1.86 (m, 2H), 1.97 (td, 1H, J=13, 3.8 Hz), 2.31 (ddd, 1H, J=14, 5.1, 3.2 Hz), 2.49 (ddd, 1H, J=12, 3.1, 1.7 Hz), 3.33 (s, 4H), 3.88 (d, 1H, J=13 Hz), 7.73 (d, 2H, J=8.8 Hz), 8.20 (d, 2H, J=8.8 Hz); $^{13}$C NMR (CDCl$_3$) δ=19.5, 23.5, 26.0, 38.3, 39.4, 42.3, 44.7, 59.3, 60.2, 65.3, 66.4, 122.9, 128.9, 143.6, 147.9, 165.6. MS (m/z) 393 (M$^+$). Anal. calcd for C$_{16}$H$_{23}$N$_3$S$_2$: C, 54.94; H, 5,89; N, 10.68, found, C, 54.87; H, 6.01; N, 10.66. HPLC: Daicel Chiralpak AD, hexane/$^i$PrOH=4/1, flow rate=1.0 mL/min: t$_R$=20.7 min (major), t$_R$=44 min (minor).

trans-3,3-Ethylenedithio-2-(p-nitrobenzoyl)indazolidine (3f): IR [cm$^{-1}$] (KBr) 3442, 3183, 1627, 1403. $^1$H NMR (CD$_2$Cl$_2$) δ=1.10 (ddd, 1H, J=12, 12, 3.8 Hz), 1.25-1.42 (m, 2H), 1.68 (m, 1H), 1.8-2.1 (m, 5H), 2.54-2.69 (m, 1H), 3.15 (td, 1H, J=11, 4.8 Hz), 3.28 (m, 1H), 3.70 (m, 1H), 3.98 (br, 2H), 7.32-7.42 (m, 3H), 7.52-7.56 (m, 2H); $^{13}$C NMR (CD$_2$Cl$_2$) δ=24.4, 25.0, 25.1, 28.6, 39.5, 42.5, 61.2, 62.3, 92.0, 127.6, 127.9, 129.6, 137.66, 166.0. MS (m/z) 320 (M$^+$). Anal. calcd for C$_{16}$H$_{20}$N$_2$OS$_2$: C, 59.96; H, 6.29; N, 8.74, found, C, 59.94; H, 6.36; N, 8.71. Daicel Chiralcel OD, hexane/$^i$PrOH=4/1, flow rate=1.0 mL/min: t$_R$=19.4 min (minor), t$_R$=30.3 min (major).

trans-3,3,6,6-Tetramethyl-2-(p-nitrobenzoyl)-perhydropyrano[3,4-c]pyrazole (3g): IR [cm$^{-1}$] (KBr) 3197, 1612, 1595, 1522, 1480, 1430, 1384, 1348, 1318. $^1$H NMR (CDCl$_3$) δ=1.24 (s, 3H), 1.2-1,3 (m, 1H), 1.29 (s, 3H), 1.48 (s, 3H), 1.56 (ddd, 1H, J=11, 11, 3.9 Hz), 1.71 (s, 3H), 1.94 (dd, 1H, J=12.3.7 Hz), 3.0 (br, 1H), 3.63 (dd, 1H, J=11, 11 Hz), 3.84 (dd, 1H, J=11, 4.1 Hz), 3.8 (br, 1H), 7.72 (d, 2H, J=8.8 Hz), 8.19 (d, 2H, J=8.6 Hz); $^{13}$C NMR (CDCl$_3$) δ=19.8, 22.9, 26.3, 31.3, 39.9, 56.4, 58.7, 60.8, 64.6, 72.5, 122.9, 128.2, 143.5, 148.0, 165.6. MS (m/z) 333 (M$^+$). Daicel Chiralcel OD, hexane/$^i$PrOH=19/1, flow rate=1.0 mL/min: t$_R$=32.6 min (major), t$_R$=37.4 min (minor).

trans-3,3'-Dimethyl-2-(p-nitrobenzoyl)-2,3,3a, 4,9,9a-hexahydro-1H-benz[f]indazole (3h): IR [cm$^{-1}$] (KBr) 3195, 1617, 1590, 1523, 1484, 1438, 1383, 1349, 1318, 1290. $^1$H NMR (CDCl$_3$) δ=1.58 (s, 3H), 1.76 (s, 3H), 1.87 (ddd, 1H, J=12, 12, 5.4 Hz), 2.58 (dd, 1H, J=15, 11 Hz), 2.9 (m, 1H), 2.91 (dd, 1H, J=16, 5.6 Hz), 3.12 (m, 1H), 3.20 (dd, 1H, J=15, 5.4 Hz), 4.04 (dbr, 1H, J=12 Hz), 7.1-7.2 (m, 4H), 7.76 (d, 2H, J=8.6 Hz), 8.20 (d, 2H, J=8.5 Hz); $^{13}$C NMR (CDCl$_3$) δ=19.7, 26.3, 28.6, 33.1, 56.3, 57.8, 65.4, 122.9, 126.4, 126.6, 128.8, 129.6, 129.7, 133.0, 134.8, 143.7, 147.9, 165.4. MS (m/z) 351 (M$^+$). Anal. calcd for C$_{20}$H$_{21}$N$_3$O$_3$: C, 68.36; H, 6.02; N, 11.96, found: C, 68.55; H, 6.05; N, 12.00. HPLC (trans isomer): Daicel Chiralpak AD, hexane/$^i$PrOH=9/1, flow rate=1.0 mL/min: t$_R$=35.9 min (major), t$_R$=41.8 min (minor).

Reference Example

Derivation of Product

A cyclic compound obtained in a [3+2] cycloaddition reaction as mentioned above is an interesting compound as it is, however, it is contemplated that the compound can be transformed into an optically active 1,3-diamine by cleaving the N—N bond as the following formula (E).

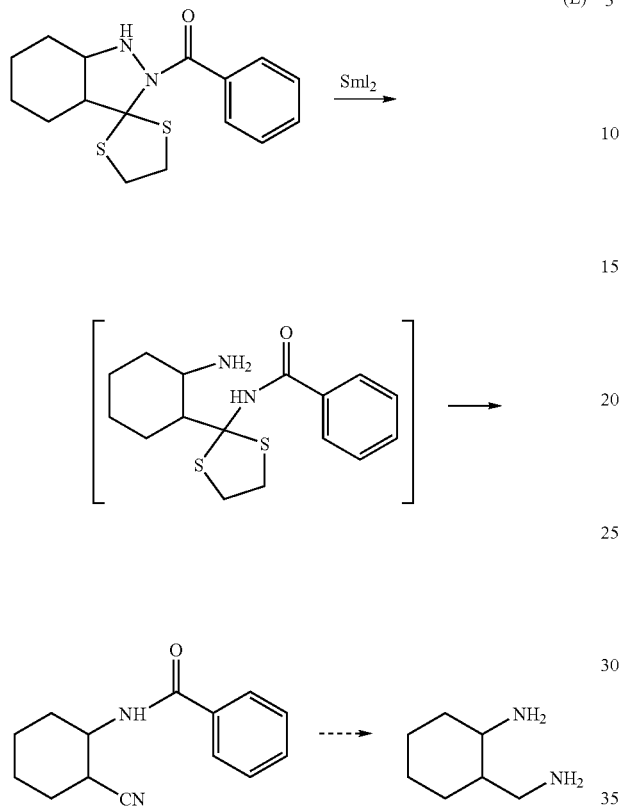

It is contemplated that these 1,3-diamines may not only enable to be used as a chiral ligand, but also enable to be applied to an analogue synthesis of an anticancer agent, cisplatin.

According to the studies by the inventors, it was found that when, for example, the following cyclic compound a was reacted with iodide samarium ($SMI_2$), a nitrile compound was produced by aftertreatment. It is contemplated that from this nitrile compound, not only aminomethylcyclohexylamine can be derived by reduction of a nitrile group and deprotection of a benzoyl group, but also a β-amino acid can be derived. Therefore, it can be said that it is a very useful compound.

INDUSTRIAL APPLICABILITY

As explained in detail above, by the invention of this application, a process for carrying out an intramolecular [3+2] cycloaddition reaction of a hydrazone under a common mild condition with a high stereoselectivity and yield can be provided. Such an asymmetric intramolecular [3+2] cycloaddition reaction has a high usability as an easy process for stereoselectively synthesizing a nitrogen-containing compound which can be found in great number in a natural product or the like.

The invention claimed is:

1. A process for an asymmetric intramolecular [3+2] cycloaddition reaction of a hydrazone which comprises reacting a hydrazone derivative represented by the following formula (III):

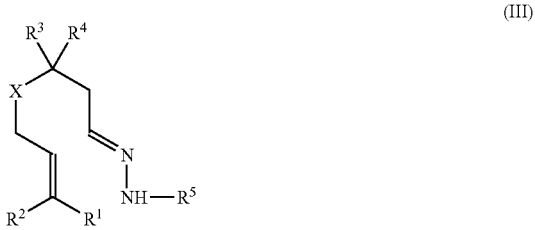

wherein $R^1$, $R^2$, $R^3$, $R^4$ and $R^5$ are each identical or different and denote a hydrogen atom or a hydrocarbon group which may have a substituent or a hetero atom, $R^1$ and $R^2$, $R^3$ and $R^4$ may be linked to form a ring by a hydrocarbon chain which may have a substituent or a hydrocarbon chain which has a hetero atom, and X denotes a hetero atom or a hydrocarbon chain which may have a substituent or a hetero atom, in the presence of an asymmetric catalyst system obtained by mixing a zirconium alkoxide represented by the following formula (I):

$$Zr(OR)_4 \quad (I)$$

wherein R is a hydrocarbon group which may have a substituent with a binaphthol derivative represented by the following formula (II):

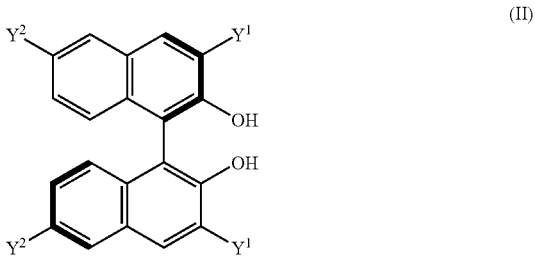

and wherein $Y^1$ and $Y^2$ are each identical or different and denote a hydrogen atom or a halogen atom, and at least one of $Y^1$ and $Y^2$ denotes a halogen atom, to produce a cycloaddition reaction product.

2. The process for an asymmetric intramolecular [3+2] cycloaddition reaction according to claim 1, which is carried out in the coexistence of a primary alcohol.

3. The process for an asymmetric intramolecular [3+2] cycloaddition reaction according to claim 2, wherein the primary alcohol is an n-propanol.

4. The process for an asymmetric intramolecular [3+2] cycloaddition reaction according to claim 1, by which an asymmetric cyclic compound represented by the following formula (IV):

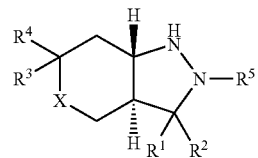

(IV)

is synthesized.

5. The process for an asymmetric intramolecular [3+2] cycloaddition reaction according to claim 1, wherein the zirconium alkoxide used in the catalyst system is $Zr(O^tBu)_4$ or $Zr(OPr)_4$.

* * * * *